United States Patent [19]

Fries

[11] Patent Number: 4,628,053
[45] Date of Patent: Dec. 9, 1986

[54] STABILIZED INJECTABLE SOLUTIONS OF PIROXICAM

[75] Inventor: Walter F. Fries, Illertissen, Fed. Rep. of Germany

[73] Assignee: Heinrich Mack Nachf., Illertissen, Fed. Rep. of Germany

[21] Appl. No.: 784,903

[22] Filed: Oct. 7, 1985

[30] Foreign Application Priority Data

Oct. 10, 1984 [DE] Fed. Rep. of Germany ....... 3437232

[51] Int. Cl.$^4$ ............................................. A61K 31/54
[52] U.S. Cl. ................................................... 514/222
[58] Field of Search ....................................... 514/222

[56] References Cited

U.S. PATENT DOCUMENTS 3,591,584  7/1971  Lombardino ...................... 260/243

4,233,299  11/1980  Trummlitz et al. ................ 424/246

FOREIGN PATENT DOCUMENTS 3217315  11/1983  Fed. Rep. of Germany .

Primary Examiner—Stanley J. Friedman
Attorney, Agent, or Firm—Charles J. Knuth; Peter C. Richardson

[57] ABSTRACT

Stable aqueous solutions of piroxicam suitable for pharmaceutical use are disclosed. These solutions all contain piroxicam in conjunction with a sub-stoichiometric amount of D-(−)-N-methylglucamine and have proplyene glycol, ethanol and water as the solvent, with the pH of said solutions being in the range of from about pH 8 to about pH 9. These particular pharmaceutical compositions possess excellent chemical stability properties and are especially suitable for parenteral administration.

6 Claims, No Drawings

STABILIZED INJECTABLE SOLUTIONS OF PIROXICAM

BACKGROUND OF THE INVENTION

This invention relates to new and useful aqueous anti-inflammatory compositions suitable for pharmaceutical formulation. More particularly, it is concerned with certain novel aqueous piroxicam solutions which all contain D-(—)-N-methylglucamine and are of value for therapeutic administration.

Piroxicam, i.e., 4-hydroxy-2-methyl-N-(2-pyridinyl)-2H-1,2-benzothiazine-3-carboxamide 1,1-dioxide, is a known non-steroidal anti-inflammatory agent described and claimed by J. G. Lombardino in U.S. Pat. No. 3,591,584. Piroxicam is sold in capsule form worldwide and it is recognized to be a potent long-acting drug that ensures an effective piroxicam blood level when administered orally once a day. However, there are times when it is desirable to administer the drug parenterally and this can often give rise to some problems, especially since piroxicam is only sparingly soluble in water and thus does not readily lend itself to the formation of solutions.

As can be readily seen from West German Offenlegungsschrift No. 3,217,315 A1, it is for this reason that it has only so far been possible to administer various oxicam derivatives (a category which includes piroxicam) via the oral route of administration. It is also known from this publication that the solubility of piroxicam can be improved slightly via salt formation with equimolar amounts of N-methyl-D-glucamine (a reaction which is also taught for certain other oxicam derivatives in U.S. Pat. No. 4,233,299). Moreover, in the case of the oxicam solutions per se, there is also the additionally serious problem concerning their physical instability so that even if such compounds or their salts dissolve in the appropriate solvent, these solutions tend to precipitate the active ingredients after a short period of time. In West German Offenlegungsschrift No. 3,217,315 A1, there is proposed a solution to this problem which involves increasing the stoichiometric base amount of 1:1 known for the production of organic salts and, if necessary, also adding a pharmaceutically acceptable organic solvent which is freely-miscible with the water. In this way, it is possible to obtain highly-concentrated solutions of piroxicam, e.g., say up to 30% by weight, which remain stable even after a long period of storage and show no separation of the active substances therefrom, especially when N-methyl-D-glucamine is used as a base. Accordingly, West German Offenlegungsschrift No. 3,217,315 A1 discloses piroxicam-containing pharmaceutical preparations, characterized in that they also contain an amount of organic base which is more than one molar with respect to piroxicam and further characterized in that N-methyl-D-glucamine is a preferred base.

The present invention is based on the finding that solutions of piroxicam, and particularly diluted aqueous solutions of same, exhibit chemical instability, i.e., piroxicam can easily be destroyed by way of hydrolysis and/or oxidation, with the assessed product of decomposition being 2-aminopyridine. Additionally, piroxicam has even been found to smell like pyridine under these same conditions. Thus, even though applicant has found that it is possible to obtain suitable injectable solutions of piroxicam by the use of a proper admixture of solvents (organic and aqueous) and the correct adjustment of the pH value in order to overcome the solubility problems of piroxicam, the chemical instability of such solutions still remains and so creates further difficulties.

SUMMARY OF THE INVENTION

In accordance with the present invention, it has now been found that stable aqueous solutions of piroxicam are provided for the first time by the addition thereto of a small, sub-stoichiometric amount of D-(—)-N-methylglucamine, i.e., the addition of the sub-stoichiometric amount of D-(—)-N-methylglucamine (which is below the known equimolar amount) considerably improves the chemical stability of piroxicam. Furthermore, it has also been found that piroxicam is freely soluble in an organic-aqueous solvent if the pH value of the solution is suitably buffered to about pH 8–9.

Accordingly, stable aqueous solutions of piroxicam are now provided for the first time by means of a novel pharmaceutical composition comprising a solution in an aqueous organic solvent mixture of piroxicam together with a sub-stoichiometric amount of D-(—)-N-methylglucamine, said solution having a pH value in the range of from about pH 8 to about pH 9. These particular solutions are all relatively very stable and parenterally well tolerated, as contrasted with the prior art piroxicam solutions in the same pH range which lack the D-(—)-N-methylglucamine component. As a result, they are especially suited for parenteral administration and can be used as injectable solutions.

More specifically, stable aqueous injectable solutions of piroxicam are now provided for the first time by means of a novel pharmaceutical composition comprising a dilute solution of piroxicam in an aqueous organic solvent system together with from about 0.2 mole to about 0.9 mole of D-(—)-N-methylglucamine per each mole of piroxicam, said solution having a pH value in the range of from about pH 8 to about pH 9.

DETAILED DESCRIPTION OF THE INVENTION

In accordance with a more detailed consideration of the invention, mixtures of organic solvents and water containing from about 40% to about 60% by volume of water have been found to be especially useful as the solvent phase for the injectable solutions. The organic solvents to be employed in this connection are the usual solvents used for injectable solutions and must necessarily be water-miscible and physiologically acceptable. Typical solvents include ethanol, propylene glycol, polyethylene glycol, dimethylformamide and diethylformamide, etc. A mixture of propylene glycol (i.e., 1,2-propanediol) and ethanol is especially preferred, with the preferred organic solvent mixture being from about 30% to about 50% by volume of propylene glycol and from about 5% to about 15% by volume of ethanol. The most preferred solvent for the injectable solutions of the present invention, i.e., the overall aqueous organic solvent, consists of about 40% by volume of propylene glycol, about 10% by volume of ethanol and about 50% by volume of water.

In such an admixture of solvents and at a pH value of pH 8, the solubility of piroxicam can easily exceed the required concentration, which is normally set at an upper limit of about 8% for the aqueous injectable solutions of the present invention. However, this high solubility generally presupposes that the solution is well-buffered and adjusted to a pH value within very narrow limits. Otherwise, if the pH deviates even slightly so as to come close to a value of pH 7, a considerable reduction in the degree of solubility will take place and possibly, even a certain amount of crystallization will occur. For this reason, it is therefore necessary to first dissolve piroxicam with the aid of a caustic soda solution and then to mix it with a phosphate buffer in order to adjust the piroxicam solution to a pH value that is in the range of from about pH 8 to about pH 9. In general, the aqueous injectable solutions of the present invention all contain piroxicam at a concentration level of from about 1% to about 8% by weight, based on the total volume of solution, although preferred concentrations will ordinarily range from about 2% to about 4% on this same basis. As previously indicated, the D-(—)-N-methylglucamine component is always present with the piroxicam in a less than stoichiometric amount and generally, from about 0.2 mole to about 0.9 mole per mole of piroxicam, with the preferred range being from about 0.5 mole to about 0.9 mole of D-(—)-N-methylglucamine per mole of piroxicam.

The physical stability of the aqueous injectable solutions of the present invention is determined in the challenge test (fluctuations between 5° C. and 25° C.), whereby such solutions are found to be physically stable over a long period of time, with no crystallization being observed even after having first been stored in a refrigerator (Ca. 6° C.) for a period of twelve months. The corresponding aqueous piroxicam solutions which lack the sub-stoichiometric amount of the D-(—)-N-methylglucamine component also possess this same degree of physical stability, but fail to exhibit the same degree of chemical stability as will hereinafter be shown and discussed in some detail.

The chemical stability of the aqueous injectable solutions of the present invention is determined by the comparative tests described below. In these tests, ampoules were filled with an injectable solution of piroxicam. The solvent contained 40% by volume of propylene glycol, 10% by volume of ethanol and 50% by volume of water, in which 20 mg. of piroxicam were then dissolved per each ml. of solvent according to the process hereinbefore described. In one case, the injectable solution was examined without the addition of D-(—)-N-methylglucamine and in the other, with the addition thereto of 0.9 mole of D-(—)-N-methylglucamine per mole of piroxicam. The ampoules were then stored at 50° C. and 75° C., and the 2-aminopyridine content of the injectable solution and the odor of same were both checked after various storage time intervals. In this way, the following results were obtained as summarized in the tables below:

TABLE I

Content of 2-Aminopyridine in Ampoules[1] Without D-(—)-N—Methylglucamine

| Temp. | Storage Time in Weeks | | | |
|---|---|---|---|---|
| | 3 | 6 | 12 | |
| 50° C. | 0.57% | 0.67% | 0.9% | |
| 75° C. | 2.31% | 7.57% | 10.5% | After 12 weeks, 63% of piroxicam was still found. |

[1]When opening the ampoules, an odor of pyridine was detected.

TABLE II

Content of 2-Aminopyridine in Ampoules[1] With the Addition of D-(—)-N—Methylglucamine

| Temp. | Storage Time in Weeks | | | |
|---|---|---|---|---|
| | 3 | 6 | 12 | |
| 50° C. | 0.01% | 0.0% | 0.0% | |
| 75° C. | 0.66% | 2.66% | 4.0% | After 12 weeks, 86% of piroxicam was still found. |

[1]When opening the ampoules, no odor of pyridine could be detected.

As the above data clearly illustrate, the ampoules containing D-(—)-N-methylglucamine are substantially more stable from a chemical point of view than those which do not contain this particular component. Further tests also show that the stabilized ampoules can be sterilized at 120° C. for a period of 20 minutes. In summary, therefore, the comparative tests show the advantageous effect achieved by adding a small amount of D-(—)-N-methylglucamine to the aqueous piroxicam solutions in order to improve their chemical stability.

Accordingly, a particularly preferred composition of the invention involves a stable aqueous injectable solution of piroxicam comprising (A) as the solvent therefor from about 30% to about 50% by volume of propylene glycol, from about 5% to about 15% by volume of ethanol and from about 40% to about 60% by volume of water, based on the total volume of the solvent, said water being present in sufficient amount to total 100%, and (B) as the essential active ingredient therein from about 1% to about 8% by weight of piroxicam, based on the total volume of solution, together with from about 0.2 mole at about 0.9 mole of D-(—)-N-methylglucamine per each mole of piroxicam, said solution having a pH value in the range of from about pH 8 to about pH 9.

EXAMPLE 1

A stable aqueous injectable solution of piroxicam was prepared by combining the following materials together in the manner indicated below:

| | GRAMS |
|---|---|
| Piroxicam | 20.0 |
| Sodium dihydrogen phosphate monohydrate | 2.5 |
| D-(—)-N—Methylglucamine | 10.0 |
| Propylene glycol | 400.0 |
| Ethanol | 100.0 |
| Sodium hydroxide | 1.0 |
| Redistilled water, sufficient to make 1 liter. | |

A 400 ml. portion of the redistilled water was initially employed, and sodium dihydrogen phosphate monohydrate and D-(—)-N-methylglucamine were then dissolved therein with the aid of constant agitation. This was then followed by the addition of propylene glycol and ethanol to the aqueous solution with continued agitation. At this point, the piroxicam was dissolved in the resulting aqueous organic solution with further continued agitation, while the pH was subsequently adjusted to a value of pH 8 with the aid of a caustic soda solution. Finally, the resultant solution was placed in a volumetric flask and brought to a total volume of 1 liter with the remaining portion of the redistilled water.

The piroxicam solution obtained in this manner was then sterilized by means of filtration through suitable filters with the aid of nitrogen gas and thereafter ampoules were filled therewith. This particular solution was found suitable for all forms of parenteral administration. During the processing of the solution and the filling of the ampoules, additional gassing with nitrogen can be applied.

EXAMPLE 2

A stable aqueous solution injectable solution of piroxicam was prepared by combining the following materials together in the manner indicated below:

|  | GRAMS |
|---|---|
| Piroxicam | 20.0 |
| Sodium dihydrogen phosphate monohydrate | 2.5 |
| D-(−)-N—Methylglucamine | 2.5 |
| Propylene glycol | 400.0 |
| Ethanol | 100.0 |
| Sodium hydroxide | 1.0 |
| Redistilled water, sufficient to make 1 liter. | |

A 400 ml. portion of the redistilled water was initially employed, and sodium dihydrogen phosphate monohydrate and D-(−)-N-methylglucamine were then dissolved therein with the aid of constant agitation. This was then followed by the addition of propylene glycol and ethanol to the aqueous solution with continued agitation. At this point, the piroxicam was dissolved in the resulting aqueous organic solution with further continued agitation, while the pH was subsequently adjusted to a value of pH 8 with the aid of a caustic soda solution. Finally, the resultant solution was placed in a volumetric flask and brought to a total volume of 1 liter with the remaining portion of the redistilled water.

The piroxicam solution obtained in this manner was then sterilized by means of filtration through suitable filters with the aid of nitrogen gas and thereafter ampoules were filled therewith. This particular solution was found suitable for all forms of parenteral administration. During the processing of the solution and the filling of the ampoules, additional gassing with nitrogen can be applied.

I claim:

1. A stable aqueous injectable solution of piroxicam comprising (A) as the solvent therefor from about 30% to about 50% by volume of propylene glycol, from about 5% to about 15% by volume of ethanol and from about 40% to about 60% by volume of water, based on the total volume of the solvent, said water being present in sufficient amount to total 100%, and (B) as the essential active ingredient therein from about 1% to about 8% by weight of piroxicam, based on the total volume of the solution, together with from about 0.2 mole to about 0.9 mole of D-(−)-N-methylglucamine per mole of piroxicam, said solution having a pH value in the range of from about pH 8 to about pH 9.

2. A solution as claimed in claim 1 wherein the solvent consists of 40% by volume of propylene glycol, 10% by volume of ethanol and 50% by volume of water.

3. A solution as claimed in claim 1 wherein piroxicam is present at a concentration level of from about 2% to about 4% by weight.

4. A solution as claimed in claim 1 wherein D-(−)-N-methylglucamine is present in an amount ranging from about 0.5 mole to about 0.9 mole of D-(−)-N-methylglucamine per mole of piroxicam.

5. A stable aqueous injectable solution of piroxicam comprising (A) as the solvent therefor about 40% by volume of propylene glycol, about 10% by volume of ethanol and about 50% by volume of water, based on the total volume of the solvent, and (B) as the essential active ingredient therein from about 2% to about 4% by weight of piroxicam, based on the total volume of the solution, together with from about 0.2 mole to about 0.9 mole of D-(−)-N-methylglucamine per each mole of piroxicam, said solution having a pH value in the range of from about pH 8 to about pH 9.

6. A solution as claimed in claim 5 wherein piroxicam is present at a concentration level of about 2% by weight and D-(−)-N-methylglucamine is present in amount that is about 0.9 mole of D-(−)-N-methylglucamine per mole of piroxicam.

* * * * *